US00PP08352P

United States Patent [19]

Zemach

[11] Patent Number: Plant 8,352

[45] Date of Patent: Aug. 17, 1993

[54] GYPSOPHILA L. VARIETY — OR

[75] Inventor: Samuel Zemach, Lev Hasharon, Israel

[73] Assignee: Rahan Meristem, Western Galilee, Israel

[21] Appl. No.: 813,856

[22] Filed: Dec. 26, 1991

[51] Int. Cl.[5] ..... A01H 5/00

[52] U.S. Cl. ..... Plt./68.1

[58] Field of Search ..... Plt./68.1, 54.1

[56] References Cited

U.S. PATENT DOCUMENTS

P.P. 384 4/1940 Starr ..... Plt. 68.1

OTHER PUBLICATIONS

Huxley, et al., (Ed.) "*Gypsophila L.*" The New R.H.S. Dictionary of Gardening, RHS, London, 1992, pp. 477–478.

*Primary Examiner*—James R. Feyrer
*Attorney, Agent, or Firm*—Synnestvedt & Lechner

[57] ABSTRACT

A new and distinct variety of *Gypsophila paniculata* L. that is particularly characterized by its broad leaves and full, ball-shaped flowers with full petal coverage, some petals of which exhibit a pink corona.

3 Drawing Sheets

BACKGROUND AND SUMMARY OF THE INVENTION

The present invention relates to the discovery and asexual propagation of a new and distinct variety of *Gypsophila paniculata* L. (a member of the Caryophyllàceae family, and sometimes called Baby's Breath). The new Gypsophila variety is a mutation of the *Gypsophila paniculata* L. variety commonly known as "Perfecta." The "mother plant" of the new *Gypsophila paniculata* L. "Or" variety was discovered in a cultivated planting of "Perfecta" plants that were growing in a nursery in Moshav Olesh, Israel, wherein the "Perfecta" variety has been grown for years as a commercial source of "Perfecta" variety plants. The soil in the nursery had been sterilized between growth seasons; thus there is no possibility that the "Or" mutation was the result of cross-breeding, and the most probable source for the mutation is a spotted mutation.

The new *Gypsophila paniculata* L. variety of this invention has been names "Or." Testing has shown the "Or" variety is stable in its distinguishing characteristics over several succeeding generations upon asexual propagation by using shoot cuttings and tissue culturing. "Or" is a decorative, graceful plant which is useful as an ornamental garden plant, and its cut flowers are useful for creating floral decorations.

BRIEF DESCRIPTION OF THE FIGURES

The accompanying drawings illustrate the new variety in full color as grown in a nursery in Kibbutz Gaaton, Western Galilee, Israel.

FIG. 1 is a picture showing plants of the "Or" variety obtained from tissue culture propagation and subsequent shoot-cuttings propagation at an early growth stage, about two months after planting. The size of the plants can be estimated by comparing it to the distance between two parallel wires, which are above the plant and spaced 20 centimeters apart; the wires are intended to support the plants at a later growth stage. As can clearly be seen in this picture, the leaves are broad and they have a straight cross-sectional shape.

BOTANICAL DESCRIPTION OF THE PLANT

Figure 2:
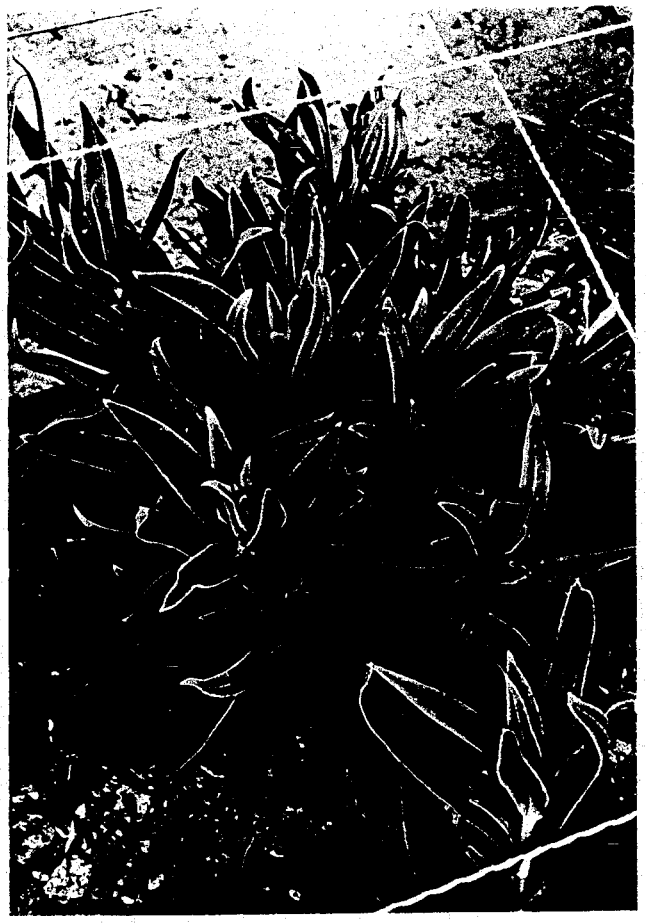
FIG. 2 is a picture showing plants of the "Or" variety at a later growth stage, about 2½ to 3 months after planting. A flowering stem prior to development of flowers thereon can clearly be seen in the center of the picture. As can be seen, the stems are green and there is noanthocyanin coloration in the stem or axil. Furthermore, the characteristic leaves of this variety can also clearly be seen in this picture (in order to obtain a size scale, as in FIG. 1, the distance between the two parallel wires, seen here between the plants, is 20 centimeters).
Figure 2:
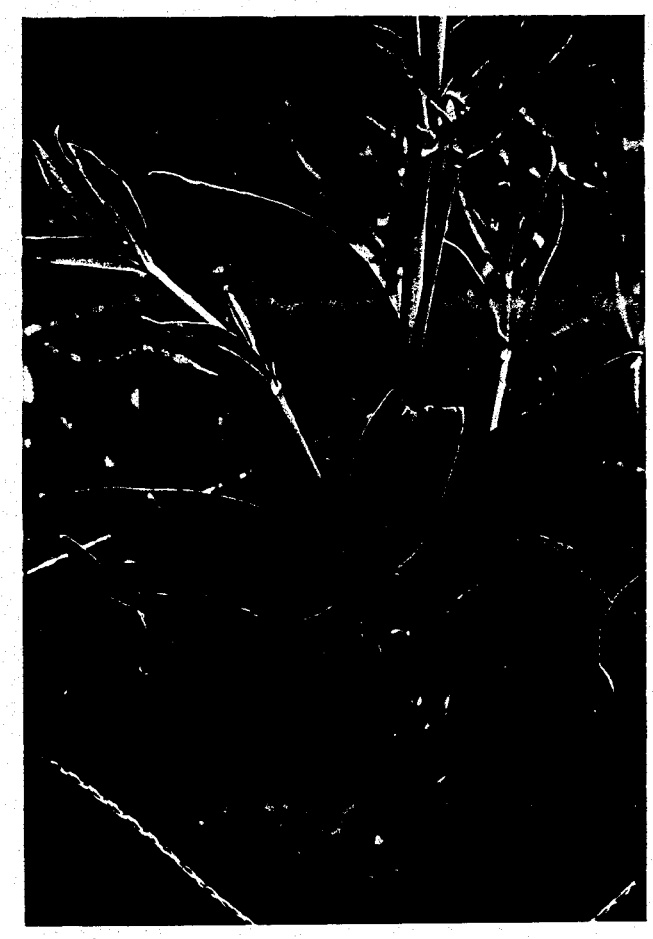
Figure 3:
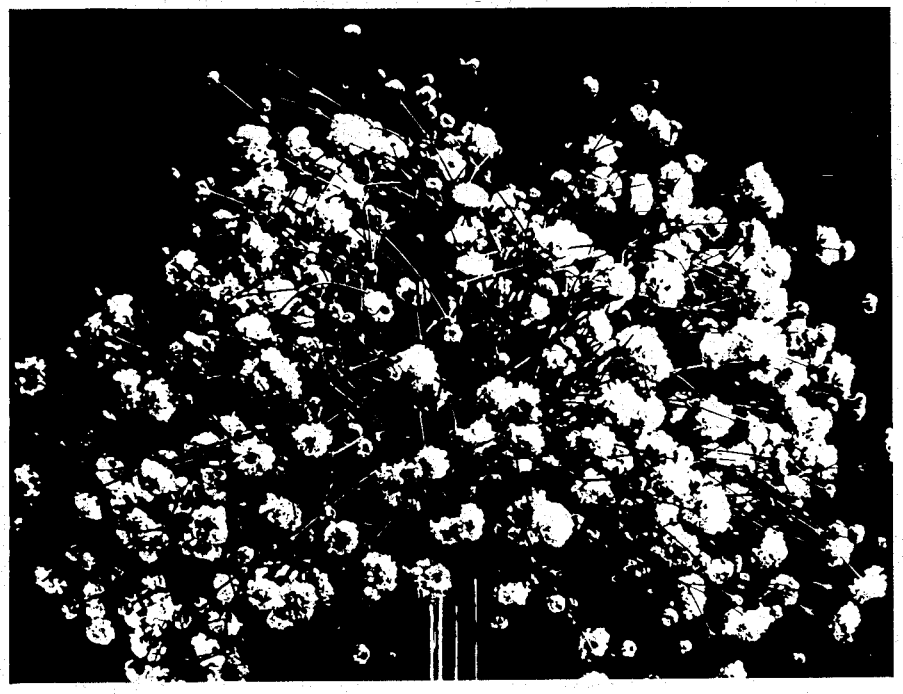
FIG. 3 shows a plurality of flowering stems with flowers in full bloom. The diameter of the fully grown flowers is about 10 mm and their general ball shape is clearly apparent. Furthermore, as can be seen, several of the petals have a pink corona which is apparent as a pink hue on the fringes of the petals of the flowers. This pink color appears in approximately 30 percent of the flowers, and always at the center of the inflorescence.

Throughout this specification, color names beginning with a small letter signify that the name of that color as used in common speech is aptly descriptive. Color names beginning with a capital letter designate values based on the R.H.S. Colour Chart published by The Royal Horticultural Society of London, England.

The descriptive matter which follows pertains to the "Or" variety of *Gypsophila paniculata* L. plants grown in Kubbutz Rosh Hanikra, Western Galilee, Israel, in Kibbutz Gaaton, Western Galilee, Israel and in Moshav Olesh, Israel, and is believed to apply to plants of the "Or" variety grown in similar conditions of soil and climate elsewhere.

The "Or" *Gypsophila paniculata* L. variety that is the subject of the present invention has, inter alia, the following features and characteristics that distinguish "Or" from other *Gypsophila paniculata* L. plants and particularly from its parent, "Perfecta" (the variety closest to "Or"). Plant features and characteristics not specifically set forth are substantially the same as that of the parent variety, "Perfecta."

The new "Or" variety is a rather tall Gypsophila plant, growing to about 1±0.2 meters. It grows taller than the "Perfecta," which grows to about 0.9±0.2 meters. The plant is rich with flowering stems, its stems freely branching from the base up, forming a globose bush at flowering time.

The "Or" plant is a medium-to-late flowering variety, flowering about 10 to 14 days later than "Perfecta" (the period of time from planting to flowering depends on the time of planting and light conditions, namely, natural or artificial). Inflorescence is diffuse and involves large panicles with corymbiform branches. The plant produces myriads of small, white flowers, resulting in a mass of delicate bloom.

The new "Or" plant produces flowers that are full and larger than that of "Perfecta." The flowers are ball-shaped and have a diameter, when fully grown, of about 10 mm. While "Or" produces larger flowers than "Perfecta," its fertility is not affected; the "Or" variety is as fertile as "Perfecta," and produces just as many flowers. No attempt was made to "produce" seed from the "Or" variety.

The number of petals in the flowers of "Or" is larger than that in "Perfecta." in "Perfecta" there are fewer petals at the center of the flower and therefore, a green coloration appears. In "Or" the petal coverage is full and so such coloration is absent. The longitudinal axis of the petals is recurved in "Or", but is straight in "Perfecta." The sepals in "Or" are larger than in "Perfecta."

The petals in "Or" are White (R.H.S. 155 D), with some having a Pink (R.H.S. 56 C) corona, while all of the petals in "Perfecta" are plain white. Petals with a pink corona become apparent as a pink hue on the fringes of the petals of the flowers. This pink color appears in approximately 30 percent of the flowers, and always at the center of the inflorescence. The pink color in "Or" is expressed stronger in the winter and spring.

One of the characteristics of most *Gypsophila paniculata* L. plants is an anthocyanin coloration of the stems. A weak anthocyanin coloration can be seen in the leaf axil of the parent variety, "Perfecta." This coloration is, however, absent from the stems of the "Or" variety.

The leaves of the "Or" plant are wide and bright, and substantially broader than those of "Perfecta." The "Or" leaves are about 22–32 mm in width, while "Perfecta" leaves are about 10–20 mm in width. The leaves of "Or" are linear-lanceolate and have a straight cross-sectional shape, while those of "Perfecta" have a concave cross-sectional shape.

The conditions for growing "Or" are generally similar to those of other *Gypsophila paniculata* L. varieties.

Culturing plant material in order to obtain a large number of microplants and plants is generally performed by micropropagation techniques, known per se. Briefly, plant buds are cut off from plants or microplants and then inserted into a growth medium such as MS-nutrient medium (Murashige, T. and Skoog, F. (1962) *Physiol. Plant* 15: 473–497). The micropropagation, in accordance with such a tissue culture growth method, requires the observing of strict sterile conditions. The cultures are grown until microplants are obtained that are suitable for further propagation or for transfer to the soil.

The microplants are then transferred each to a separate flower pot in an air-conditioned, insect-proof room. The flower pots may contain a bed of tuff in which case nutrition is provided to the plants through the irrigation system.

In the next stage, the plants are transferred to a nursery where they may also be grown in a tuff bed. The plants in the nursery are propagated and used to found the "mother plantation." The propagation in order to obtain the "mother plantation" and subsequently in order to obtain large number of plants may be vegetative shoot cuttings, namely by the regeneration of plant from shoots cut from a mother plant.

I claim:

1. A new and distinct variety of *Gypsophila paniculata* L. plant named "Or" as herein illustrated and described.

* * * * *